United States Patent [19]
Yoshizawa

[11] Patent Number: 6,050,149
[45] Date of Patent: Apr. 18, 2000

[54] DEVICE FOR MEASURING BENDING STRENGTH OF SHEET MATERIAL

[76] Inventor: Akinori Yoshizawa, Nagaoka, Japan

[21] Appl. No.: 09/299,329
[22] Filed: Apr. 26, 1999

Related U.S. Application Data

[63] Continuation of application No. 08/643,603, May 6, 1996, abandoned.
[51] Int. Cl.[7] ...................................................... G01N 3/20
[52] U.S. Cl. ............................................. 73/849; 73/812
[58] Field of Search ........................... 73/812, 813, 818, 73/826, 828, 849, 851, 854

[56] References Cited

U.S. PATENT DOCUMENTS

| | | | |
|---|---|---|---|
| 5,178,017 | 1/1993 | Dinzburg | 73/849 |
| 5,297,440 | 3/1994 | Rizk et al. | 73/849 |
| 5,419,202 | 5/1995 | Howard et al. | 73/849 |
| 5,574,227 | 11/1996 | Allan | 73/849 |
| 5,606,134 | 2/1997 | Stieber | 73/849 |

FOREIGN PATENT DOCUMENTS

| | | |
|---|---|---|
| 27 45 182 | 4/1977 | Germany. |
| 41 36 432 | 5/1993 | Germany. |

*Primary Examiner*—Max Noori
*Attorney, Agent, or Firm*—Huntley & Associates

[57] ABSTRACT

A device for measuring the natural bending strength of a sheet material, and for measuring the bending strength of a creased or scored portion of the sheet material, and for dynamically analyzing such test results. The device has a rotatable clamp, a load sensor, a data processing unit, and a data displaying unit. The load sensor is positioned to directly contact the sheet material being held by the clamp. The clamp and sheet material can be rotated so that the sheet material presses against the load sensor, and the data processing unit will then determine the resistance force detected by the load sensor and will determine the amount of rotation associated with that force, and the resulting data are then processed, stored, and can be displayed as output data in a predetermined form.

13 Claims, 11 Drawing Sheets

| DATA NO. | YIELD gf | ANGLE deg | INIT. GRAD. gf/deg |
|---|---|---|---|
| 1 | 423.9 | 17.3 | 48.9 |
| 2 | 410.7 | 16.7 | 49.1 |
| 3 | 425.8 | 18.0 | 48.3 |
| 4 | 407.8 | 17.7 | 49.5 |
| 5 | 408.3 | 17.0 | 49.3 |
| 6 | 425.8 | 17.3 | 50.2 |
|  |  |  |  |
|  |  |  |  |
|  |  |  |  |
|  |  |  |  |
| AVG. | 417.1 | 17.3 | 49.2 |
| DEV. | 9.0 | 0.5 | 0.6 |

SAMPLE: Paperboard CD
MATERIAL: Cost 310
LENGTH: 10 mm
WIDTH: 35 mm
DATA: 1995/10/18
DATA: 6

FIG. 9

| DATA NO. | YIELD gf | ANGLE deg | INIT. GRAD. gf/deg |
|---|---|---|---|
| 1 | 268.8 | 32.3 | 17.4 |
| 2 | 261.0 | 29.0 | 19.3 |
| 3 | 286.4 | 30.7 | 19.6 |
| 4 | 288.6 | 30.3 | 19.3 |
| 5 | 263.0 | 32.3 | 16.7 |
| 6 | 267.1 | 32.7 | 17.7 |
| 7 | 271.3 | 31.3 | 18.6 |
| | | | |
| | | | |
| AVG. | 272.3 | 31.2 | 18.4 |
| DEV. | 10.9 | 1.3 | 1.1 |

SAMPLE: Paperboard MD
MATERIAL: Cost 310
LENGTH: 10 mm
WIDTH: 35 mm
DATA: 1995/10/18
DATA: 7

DEVICE FOR MEASURING BENDING STRENGTH OF SHEET MATERIAL

CROSS REFERENCE TO RELATED APPLICATION

This is a Continuation of application Ser. No. 08/643,603, filed May 6, 1996, now abandoned.

BACKGROUND OF THE INVENTION

The present invention relates to a device for measuring the bending strength of sheet material such as corrugated fiberboard or paperboard, at a creased, scored, or blank portion thereof.

Typically, to manufacture containers, suitable sheet material can be subjected to a printing process and cut into a desired shape by means of a die board. The die board can also make slits, scores or creases, which aid in the formation of a container by reducing the force necessary to bend the sheet into a desired configuration. Typically, the creased portions of a sheet material can be guide lines for folding the sheet material and creating flaps from portions of the sheet material, which can then be configured or folded to make a box or other type of container.

Regarding the various means of creasing or scoring the sheet material, the warping force of the creased portion varies with the methods selected for making the crease. For example, when a crease is prepared as a series of holes by means of a laser beam, the warping force of the creased portion varies with the differences in size of each hole and with the differences in spacing between adjacent holes. The warping force of the creased portion also varies with the clearance between the edge portion of the sheet and the portion to be folded or creased. In addition, the warping force of the creased portion also varies with the materials used in the corrugated fiberboard and with the conditions of the formed crease.

As a consequence of the aforementioned variations in the warping force of the creased portion, the following problems can occur. In a case where the boxes are used for packing a wide variety of products on packing lines under automatic control, the step of fixing the top and bottom flaps of packing box together by adhesive tape is performed as a last step in the packing process. The height of the empty box depends on the warping force of the creased portion, the box's own weight, and the symmetry or proportion of the box's shape or dimensions. When the warping force of the creased portion is too high, each flap of the corrugated box tends to extend higher than the acceptable height a or width of the box with respect to the packing line. If the flaps of the corrugated box extend too high, it is difficult to place the box correctly on the line and to prevent it from becoming entangled with equipment along the line, which may cause the packing line to be stopped.

Recently, automatic high-speed packaging apparatuses have been introduced in the food and drink industries, and containers made of paperboard or corrugated fiberboard used in those fields can suffer serious damage depending on the quality of the creases formed thereon. Accordingly, manufacturers of paper containers and corrugated fiberboard have tried to develop a quality control method with a particular emphasis on the strength of the crease.

The strength of any portion of the sheet material, except the creased portion, is directly related to the strength of the resulting container. It is therefore important to understand the bending strength of the sheet material independent of the bending strength of the creased portions of the sheet material, so that the relationship between the two can be established for each type of sheet material, and from the point of quality control.

SUMMARY OF THE INVENTION

The present invention provides a device for measuring the bending strength of various sheet materials and for measuring the bending strength of creased or scored portions thereof. In addition, the present invention provides a portable device for measuring the bending strength of sheet material.

Specifically, the present invention provides a device for bending sheet material and measuring the force required to naturally crease the material as it is bent, comprising: a clamp for securing one end of the sheet material, the clamp having a tip that extends perpendicularly to the predetermined bending direction; a load sensor positioned to contact a portion of the sheet material; a means for rotating the clamp; a means for determining the angle of clamp rotation necessary to cause the sheet material to crease; a means for measuring the force required to naturally crease the sheet material by dynamically analyzing data obtained from the load sensor and the means for determining the angle of clamp rotation; and a means for displaying the data. The present invention also provides a portable device as described above.

By using the device of the present invention, bending strength of corrugated fiberboard, paperboard, or a creased or scored portion thereof, can be easily measured in any location at any time. Accordingly, the device of the present invention contributes to the control of qualities of these sheet materials and also facilitates sales thereof. The above and other objects, effects, features, and advantages of the present invention will become more apparent from the following description and the accompanying figures.

DETAILED DESCRIPTION OF THE INVENTION

The present invention will be described in detail with respect to preferred embodiments, and changes and modifications may be made without departing from the invention in its broader aspects. Accordingly, it is the intention to cover all such changes and modifications as fall within the true spirit of the invention.

Figure 1:
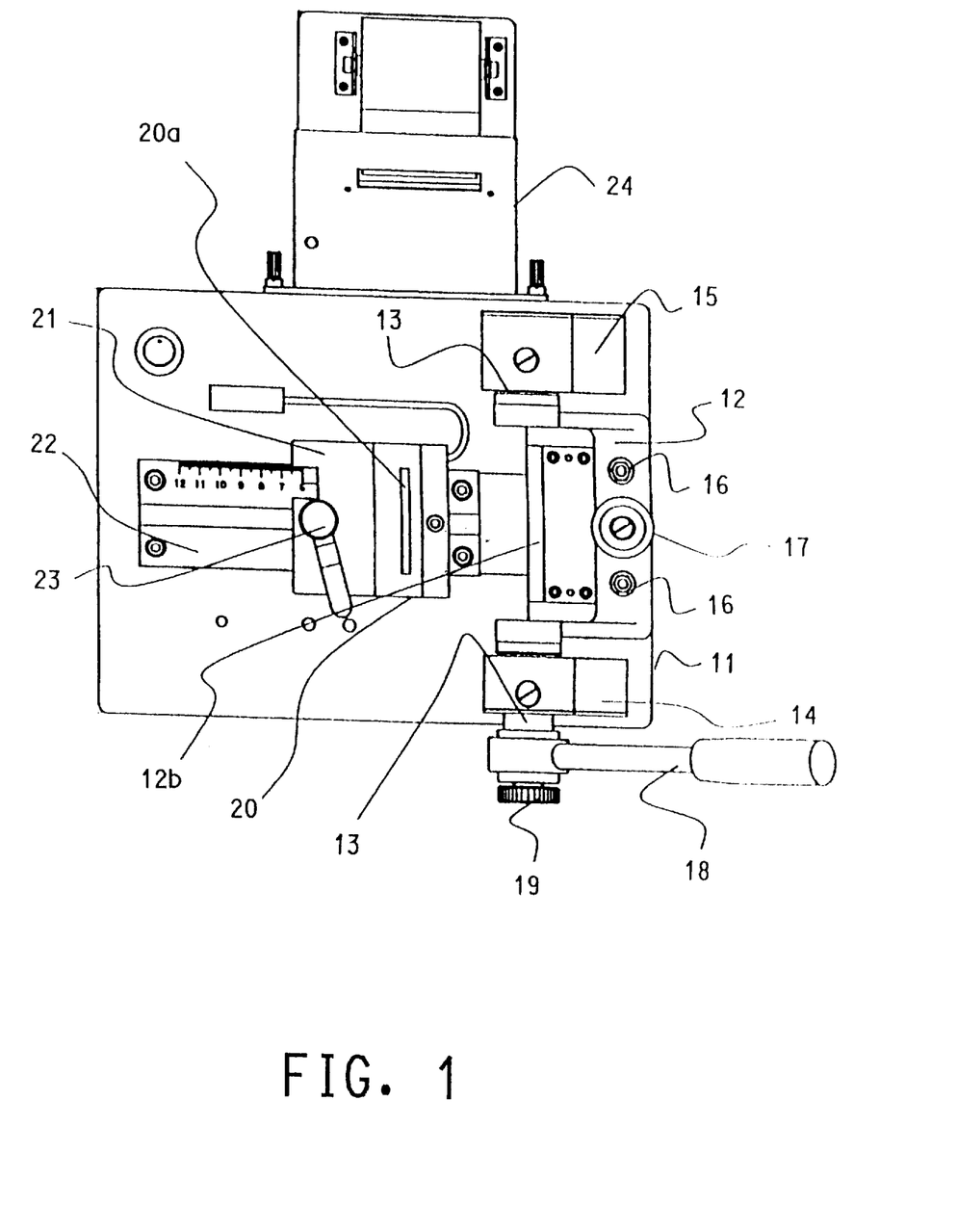
FIG. 1 is a top plan view of a first embodiment of a device of the present invention for measuring the bending strength of sheet materials.
Figure 2:
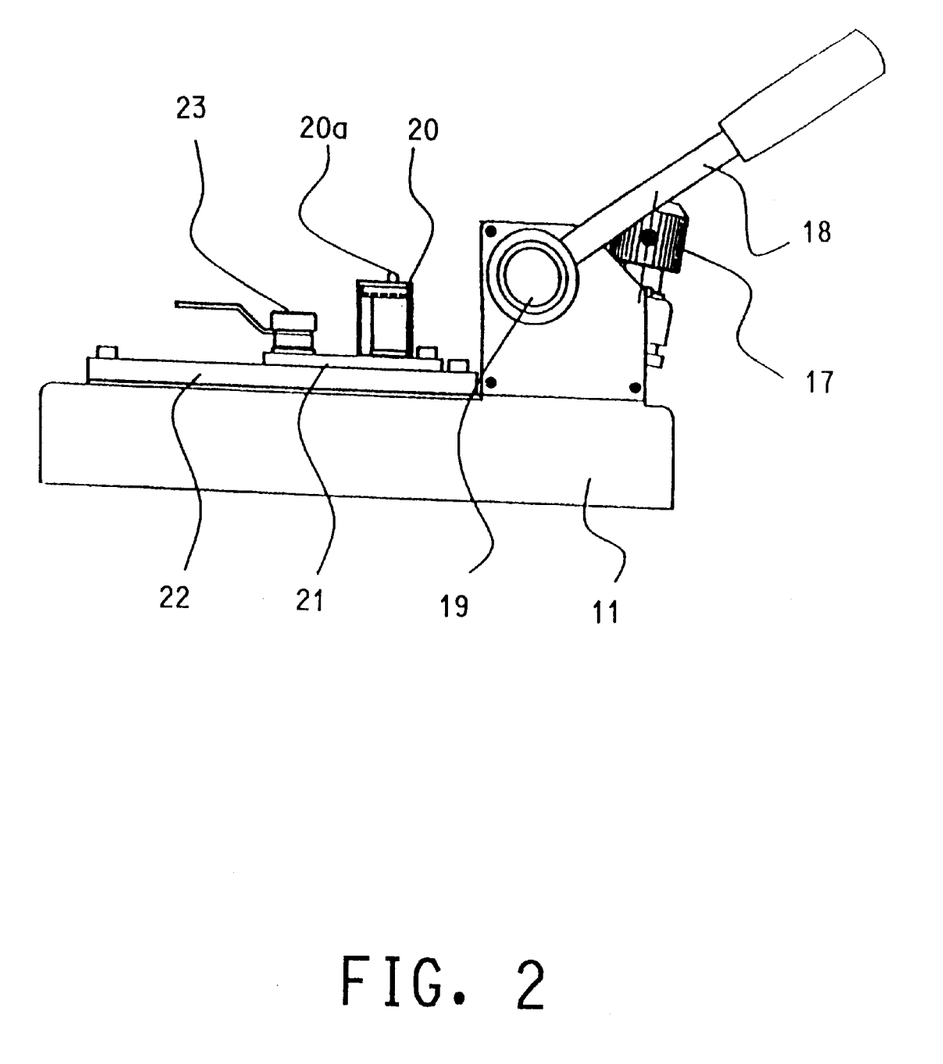
FIG. 2 is a front elevational view of the device of FIG. 1.
Figure 3:
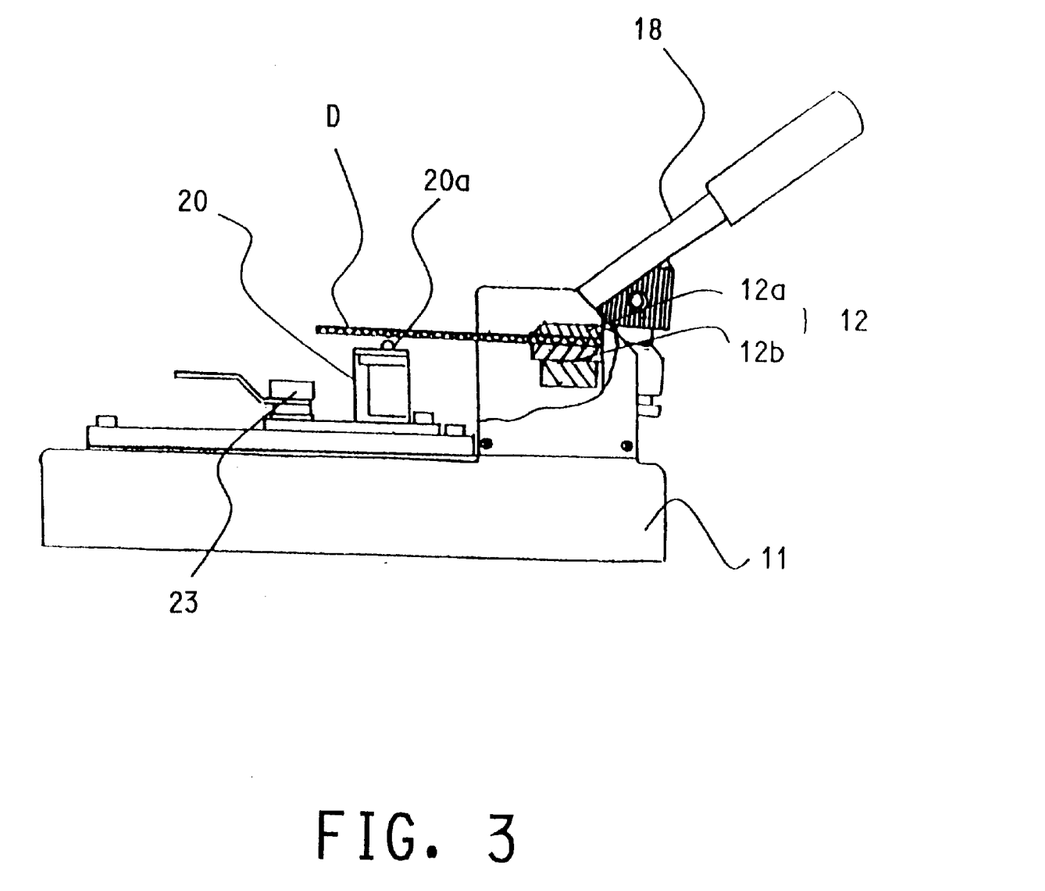
FIG. 3 is a front elevational view of the device of FIG. 1 partially cutaway to show a sample sheet material.

FIGS. 1 to 3 illustrate a first embodiment of a device of the present invention for measuring bending strength of a sheet material. In these figures, FIG. 1 is a top plan view, and FIGS. 2 and 3 are front elevational views of an embodiment of a device of the present invention. The device shown in these figures is compact and lightweight so as to be easily carried or moved to any place at any time.

As shown in FIGS. 1 to 3, the device comprises a base 11 in which a data processing unit (not shown) is embedded. The data processing unit is provided for processing the results obtained by measurement to print them as characteristic values including a yielding value (gf), a yielding angle (deg), an initial gradient (gf/deg), and a graph representing the relationship between a revolution angle (deg) and a resistance value (gf). On one portion of the base 11, there is provided a clamp 12 for clamping one end of the corrugated fiberboard D as a test sheet. The clamp 12 is rotatably connected to a shaft 13 as the center of the rotation. In addition, the shaft 13 is rotatably supported by bearing pads 14, 15 which are fixed on both sides of the clamp. The clamp 12 comprises a fixed click 12a being secured to the shaft 13 and a movable click 12b that performs closing and opening with respect to the fixed click 12a. The movable click 12b is supported by a pair of pins 16 and a clamp-adjusting screw 17 so as to be movable only in the direction of opening and closing. Thus the movable click 12b can be opened or closed by revolving the clamp adjusting screw 17. The clamp 12 of the present embodiment is a ratchet type clamp that can be adjusted so the force exerted on the movable click 12b toward the fixed click 12a does not exceed a predetermined level. The adjustment of the clamp prevents the corrugated fiberboard D held therein from becoming compressed or deformed.

As shown in FIGS. 1 to 3, one end portion of the shaft 13 protrudes from the bearing pad 14 and is operatively connected to a handle 18 for revolving the clamp 12. The handle 18 can be fixed to an end portion of the shaft 13 in the direction of revolution by means of a handle-fixing screw 19. Near the center of the base 11, there is provided a load sensor 20 having a load sensing portion 20a. As shown in the figures, the load sensor 20 protrudes upward from the surface of the base 11, while the load sensing portion 20a extends in the direction corresponding to the width of the test sheet. Furthermore, the load sensor 20 is secured on a mobile platform 21 which can be moved along a guide rail 22 toward either side of the device. After the movement, the mobile platform 21 can be fixed at a predetermined position by means of a fixing screw 23.

For measuring bending strength of the corrugated fiberboard by using the device described above, a sample test sheet of corrugated fiberboard, with a size of 50 mm in width and a measuring length of 40 mm or more in length, was prepared. Then one end thereof is held by the clamp 12. In this condition, the handle 18 is in the position shown in FIGS. 2 and 3, while the free end portion of the test sheet D is in the position above the load sensing portion 20a of the load sensor 20 so as to be spaced therefrom (see FIG. 3). Then the handle 18 is revolved in a predetermined angle between about 90° and about 180° in a counterclockwise direction. As the handle 18 starts to revolve, the end of the test sheet D touches the load sensing portion 20a of the load sensor 20. The measurement can be completed by further revolving the handle in the predetermined angle from that position. A force f(a resistance value) applied on the load sensor 20 is measured so as to correspond to the revolving angle, which can be determined by an angular displacement sensor, not shown.

According to the present embodiment, as shown in FIGS. 1 to 3, there is provided a printer 24 on the opposite side of the base 11 with respect to the handle 18 equipped thereon. The printer 24 is able to print out the results processed by the aforementioned data-processing unit in accordance with the data obtained by the measurement. The results may be printed out in the form of a table showing the characteristic values or as a graph showing the relation between the revolution angle (deg) and the resistance value (gf). The printer 24 is detachable and attachable for portability. The connector for the printer 24 is in the type of RS-232C for general purpose use, so that it can be connected to a personal computer for the purpose of not only easily displaying at-a-glance charts of the characteristic values and the characteristic graphs as shown in the figures, but also for editing, comparing, and storing the data, and for easily carrying out an advanced analysis thereof.

For the sake of attaining the objectives of the present invention, with or without the printer, the device is preferably equipped with a means for displaying the data in any location at any time. For example, a data displaying device such as a liquid crystal display can be used.

Figure 4:
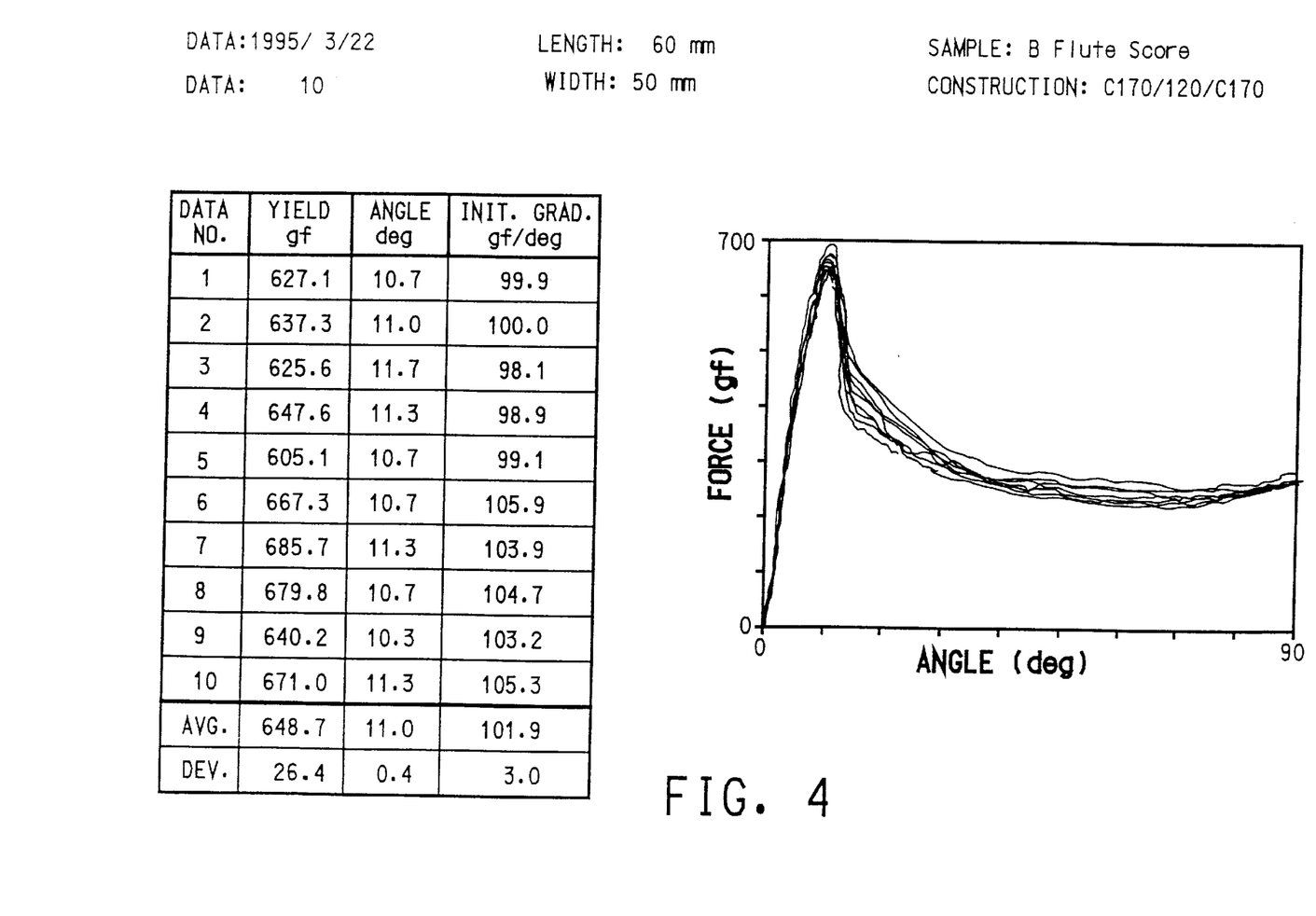
FIG. 4 is a graphical representation with a table of the results obtained by the measurement performed by the device of FIG. 1.
Figure 5:
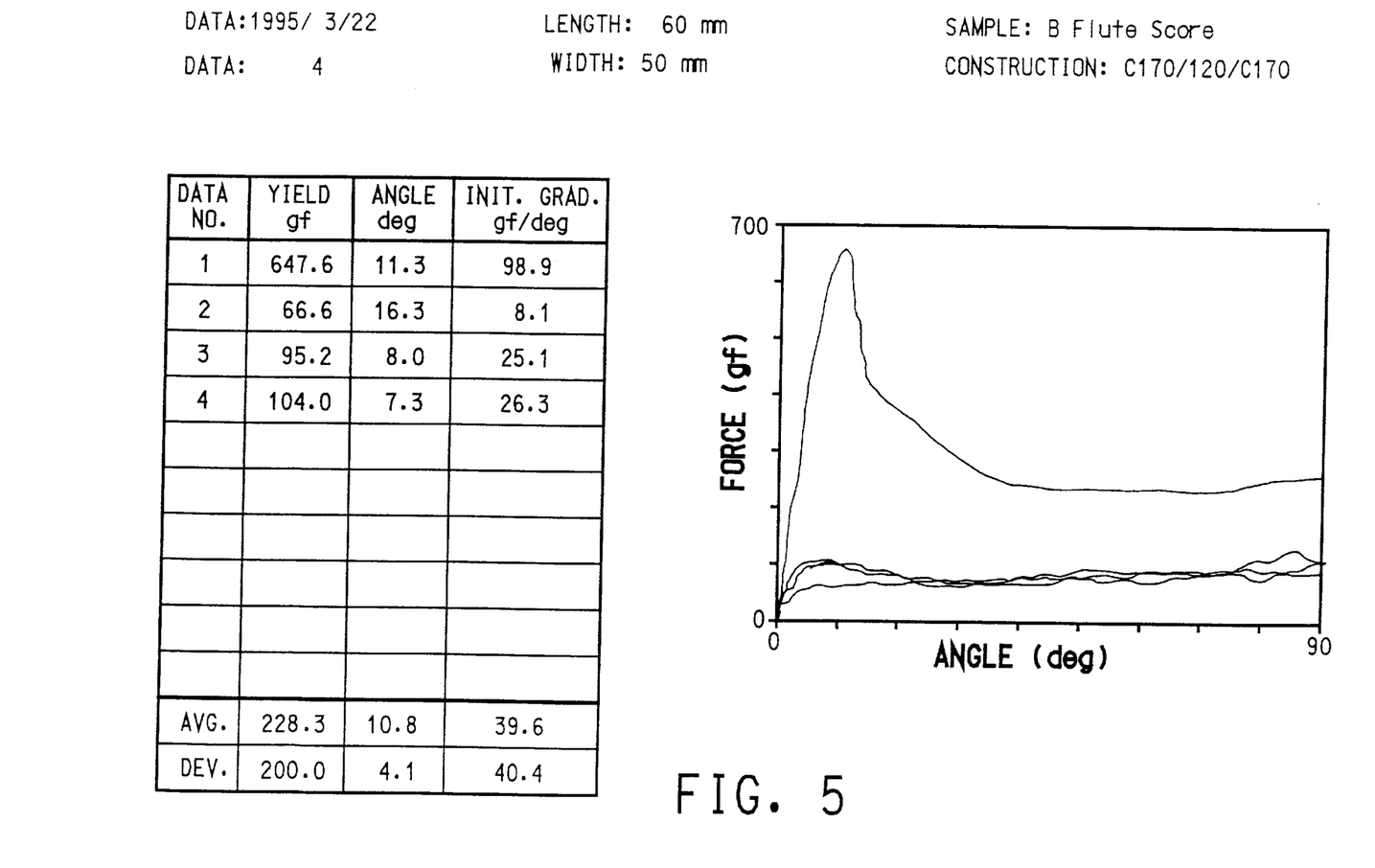
FIG. 5 is a graphical representation of the results obtained by the measurement performed by the device of FIG. 1.
Figure 6:
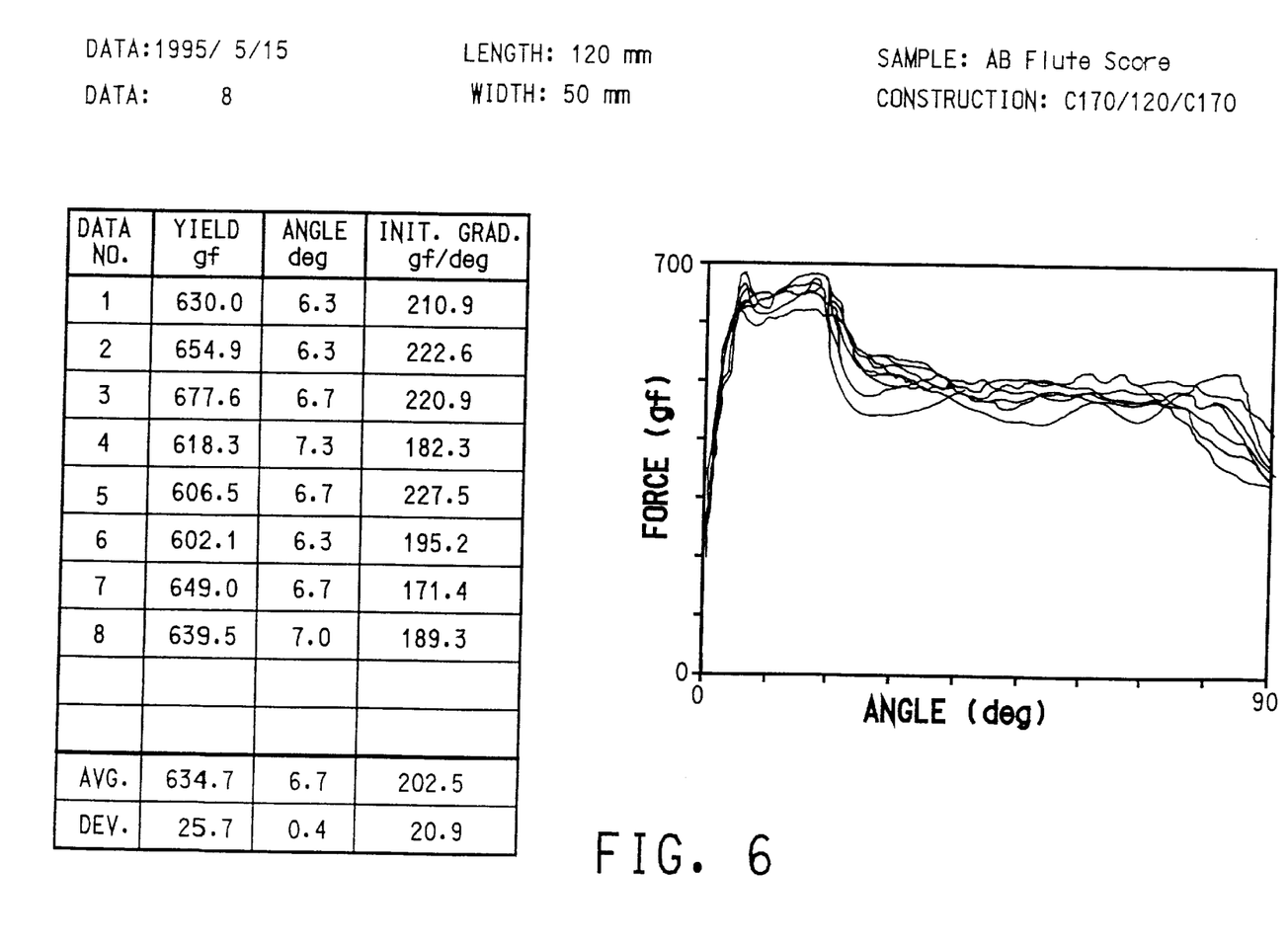
FIG. 6 is a graphical representation of the results obtained by the measurement performed by the device of FIG. 1.

Measurements for determining the bending strength of the corrugated fiberboard were performed using the device of the present invention. In addition, a plurality of obtained results of several samples were entered into a personal computer for data processing to make an assessment of bending strength. For further consideration, several examples of the output from the personal computer are shown in FIGS. 4 to 6. The results obtained from the bending measurements are shown in the tables of FIGS. 4 to 6 and include a yielding value (gf), a yielding angle (deg), and an initial gradient (gf/deg). In addition, FIGS. 4 to 6 show a graph representing the relationship between a revolution angle (deg) and a resistance value (gf).

In FIGS. 4 to 6, the following characteristic values are defined as follows.

Yielding Value (gf)

The yielding value represents a load at the time of bending the sheet material by revolving the handle from the position where the test sheet is horizontal or nearly horizontal after placing the test sheet in the measuring device. In addition, the yielding value is dependent on the stiffness of the material, so that higher the stiffness of the sheet material, the more likely it becomes that the higher yielding value has been attained. As for the corrugated fiberboard, the yielding value may vary according to, among other things, the effect of bonding conditions (i.e., bonding requirements, amount of applied paste, or the like).

Yielding Angle (deg)

The yielding angle represents an angle corresponding to the yielding value. In the process of bending the blank sheet, the higher the stiffness of the sheet material, the more likely a lower yielding angle has been attained.

Initial Gradient (gf/deg)

The initial gradient represents variations in the resistance from the time the measurement is started (i.e., at the time the revolution angle is almost at zero) to the time that the material yields to form a crease. The initial gradient is calculated from the gradient of the tangent to the line representing the test data on the graphs between the point at the beginning of the line representing where the measurement is started and the point on the line representing the formation of the crease, or when the yielding angle is attained. Therefore, the initial gradient can be obtained with respect to the bending of the corrugated fiberboard, paperboard, or the like, so that it represents the relative ease or difficult in bending (i.e., bending strength).

FIG. 4 shows the data from the measurement of the bending strength of blank portions (not the creased portions) of ten test sheets (5.0 cm in width). The measuring length of the blank portions of the sample test sheets used to obtain the data in this Figure was 6.0 cm, which corresponds to the distance between the tip of the click portion 12a and 12b of the clamp 12 and the load sensing portion 20a of the load sensor 20. The blank portion of each test sheet (class B) was scored in a direction perpendicular to a flute.

The data shown in FIG. 5 corresponds to the results of the measurement of the bending strength of the creased portion of each test sheet (5.0 cm in width and 6.0 cm in measuring length), in which data No. 1 represents the measurement at the blank portion, while data Nos. 2 to 4 represent the measurement of the creased portions of the corrugated fiberboard (class B).

The data shown in FIG. 6 corresponds to the results of the measurement of the bending strength of the scored portion of each test sheet (5.0 cm in width and 12.0 cm in measuring length) prepared from the corrugated fiberboard (class B). For the measurements detailed in FIG. 6, eight samples were used.

Figure 7:
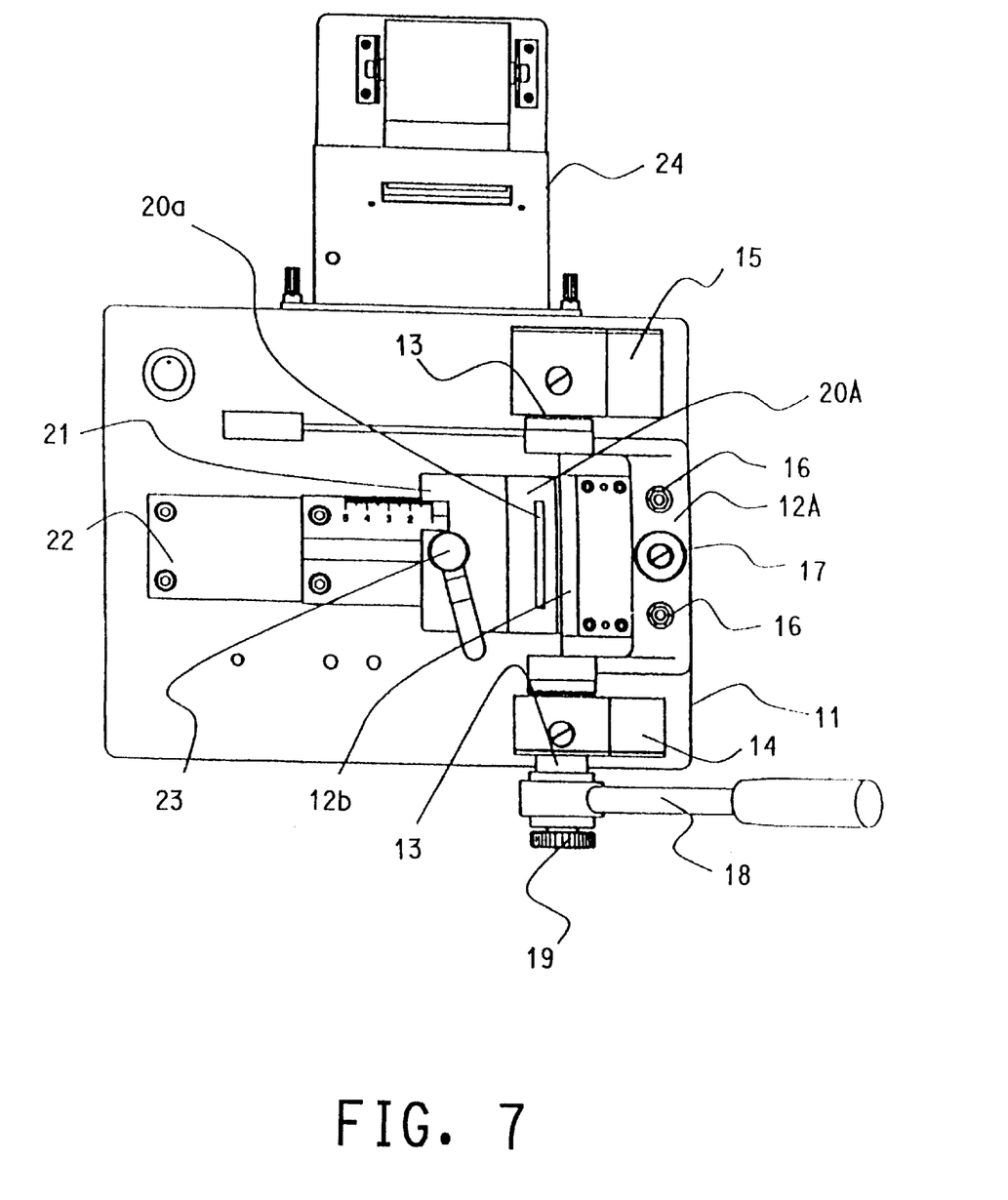
FIG. 7 is a top plan view of a second embodiment of a device of the present invention for measuring bending strength of sheet materials.

For measuring the bending strength of paperboard, FIG. 7 shows a second embodiment of a device of the present invention. The measuring device of FIG. 7 is constructed in the same way as that of the aforementioned embodiment with the exception that follows. In the second embodiment an allowable load of the load sensor 20A is maintained within narrow limits and also the load sensor 20A is positioned at a point closer to the clamp 12A, compared with that of the first embodiment. In addition, the clamp 12A of the second embodiment is not a ratchet type but a normal clamp.

FIGS. 8 to 11 represent the results of the measurement of the bending strength of samples of paperboard by using the device shown in FIG. 7. The characteristic values and definitions set forth with respect to FIGS. 4 to 6 above are applicable to these figures.

Figure 8:
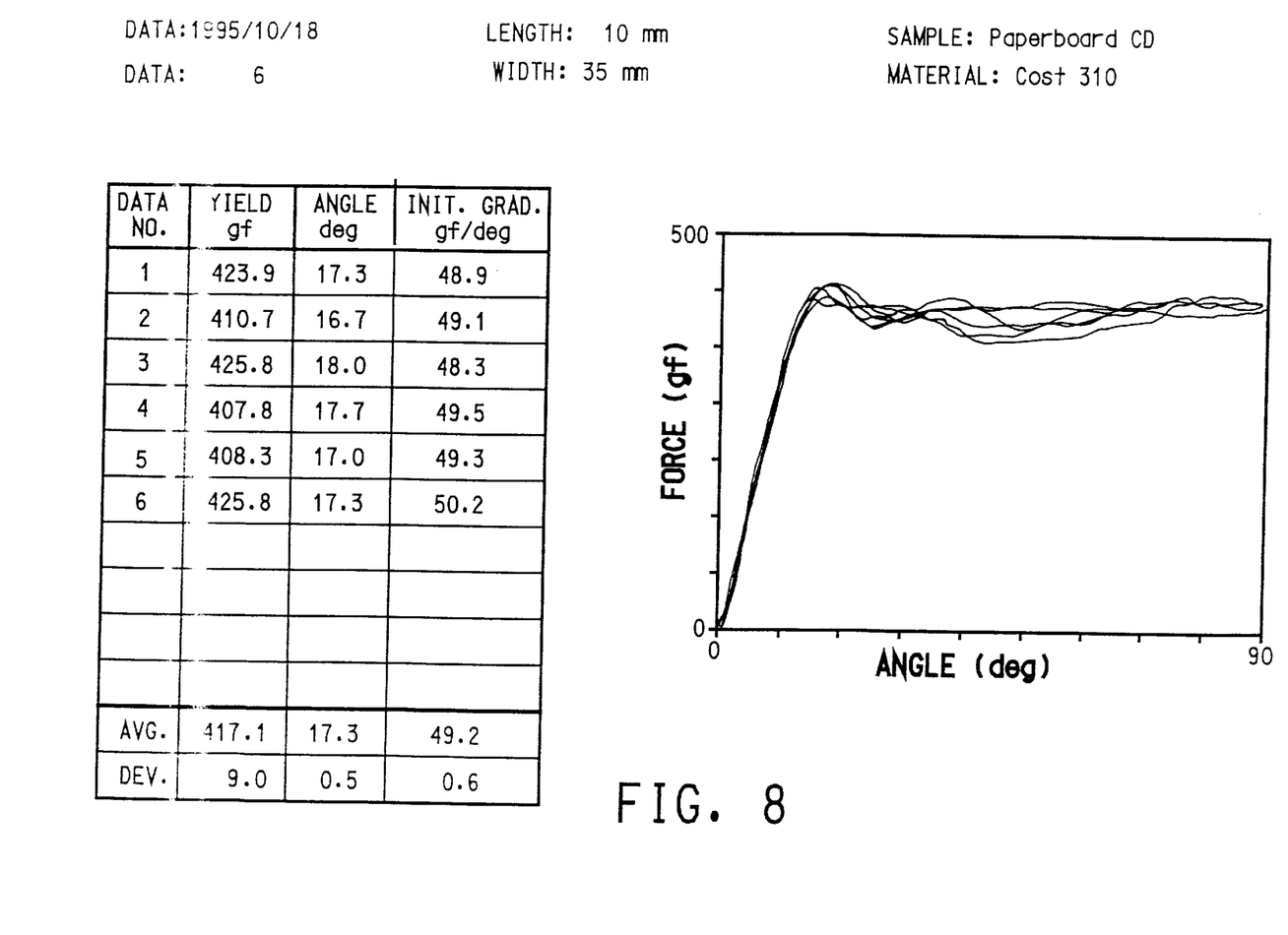
FIG. 8 is a graphical representation of the results obtained by the measurement performed by the device of FIG. 7.

FIG. 8 shows the results of the measurement of eight test sheets of paperboard having a width of 2.5 cm and a length of 1.5 cm that were bent and measured using the device of FIG. 7.

Figure 9:
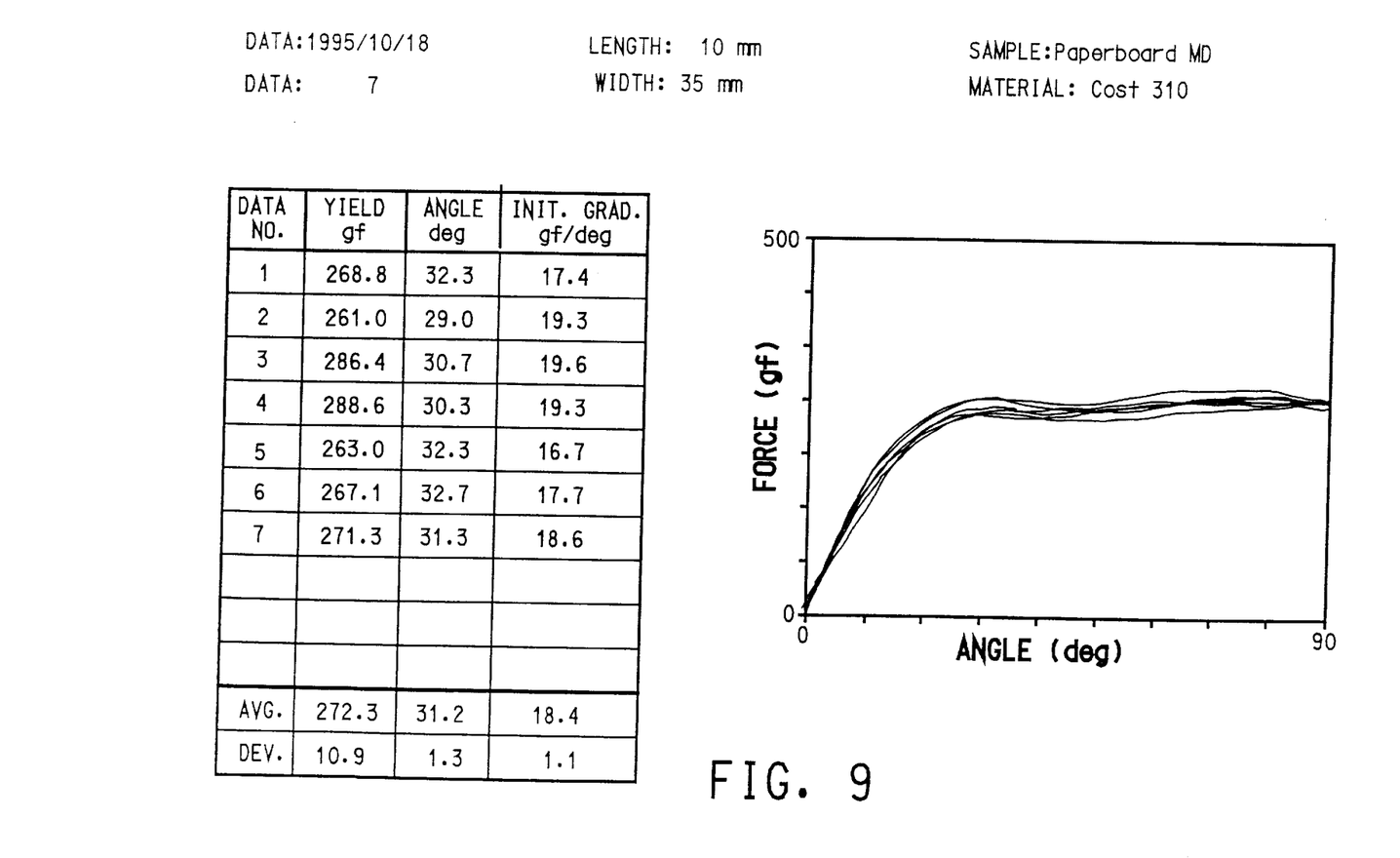
FIG. 9 is a graphical representation of the results obtained by the measurement performed by the device of FIG. 7.

FIG. 9 shows the results of the measurement of nine test sheets having a length of 1.5 cm and a width of 2.5 cm that were bent and measured with the device of FIG. 7. In FIG. 9, the test sheets were bent so that a portion of each sheet was in a parallel position with respect to cross-grain.

Figure 10:
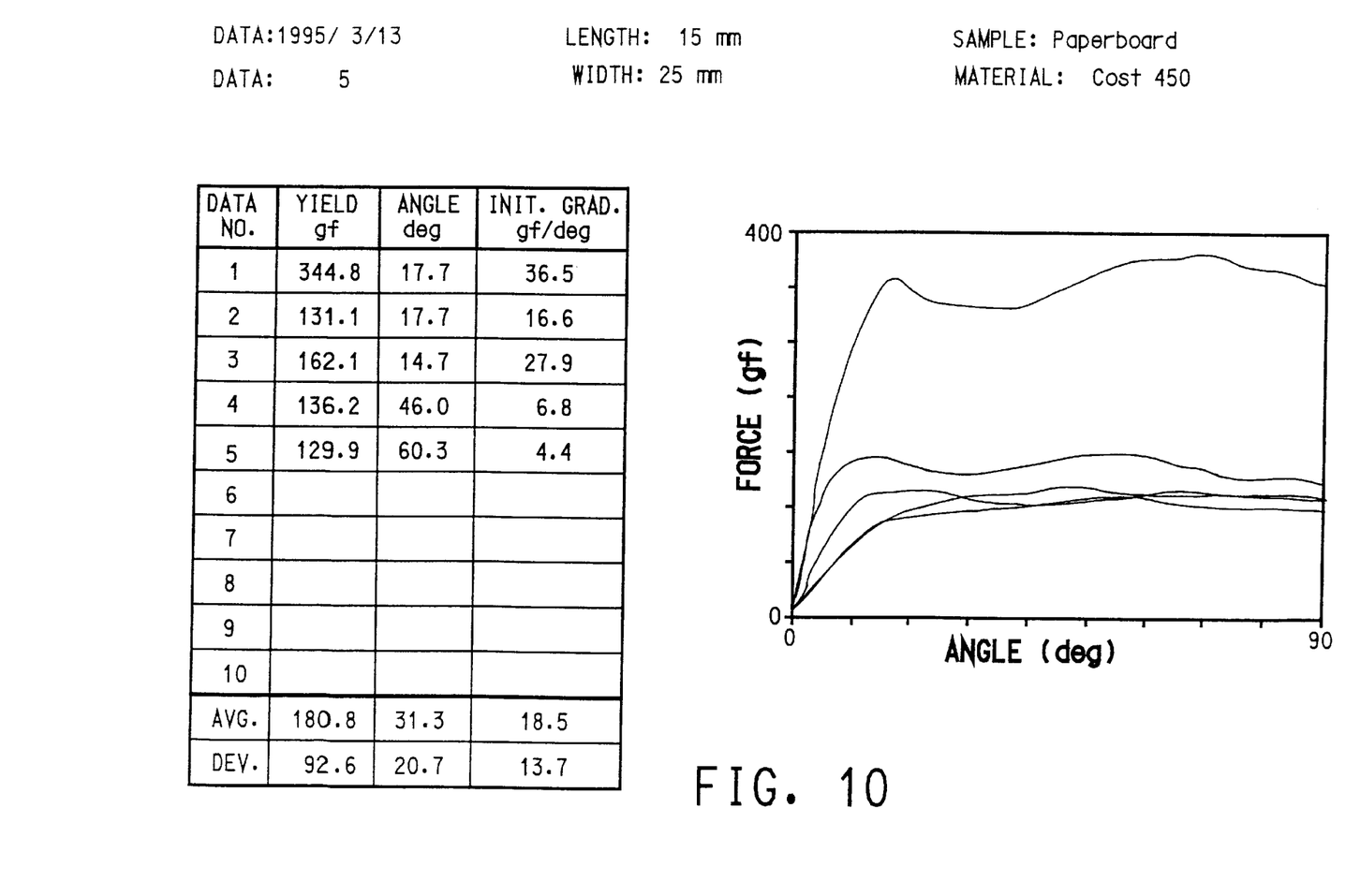
FIG. 10 is a graphical representation of the results obtained by the measurement performed by the device of FIG. 7.

FIG. 10 shows the results of the measurement under the same conditions as that of FIG. 8 except that the results were obtained by measuring bending strength of the blank portion (data No. 1), creased portion (data Nos. 2 and 3), and perforated portion (data Nos. 4 and 5) of the paperboard.

Figure 11:
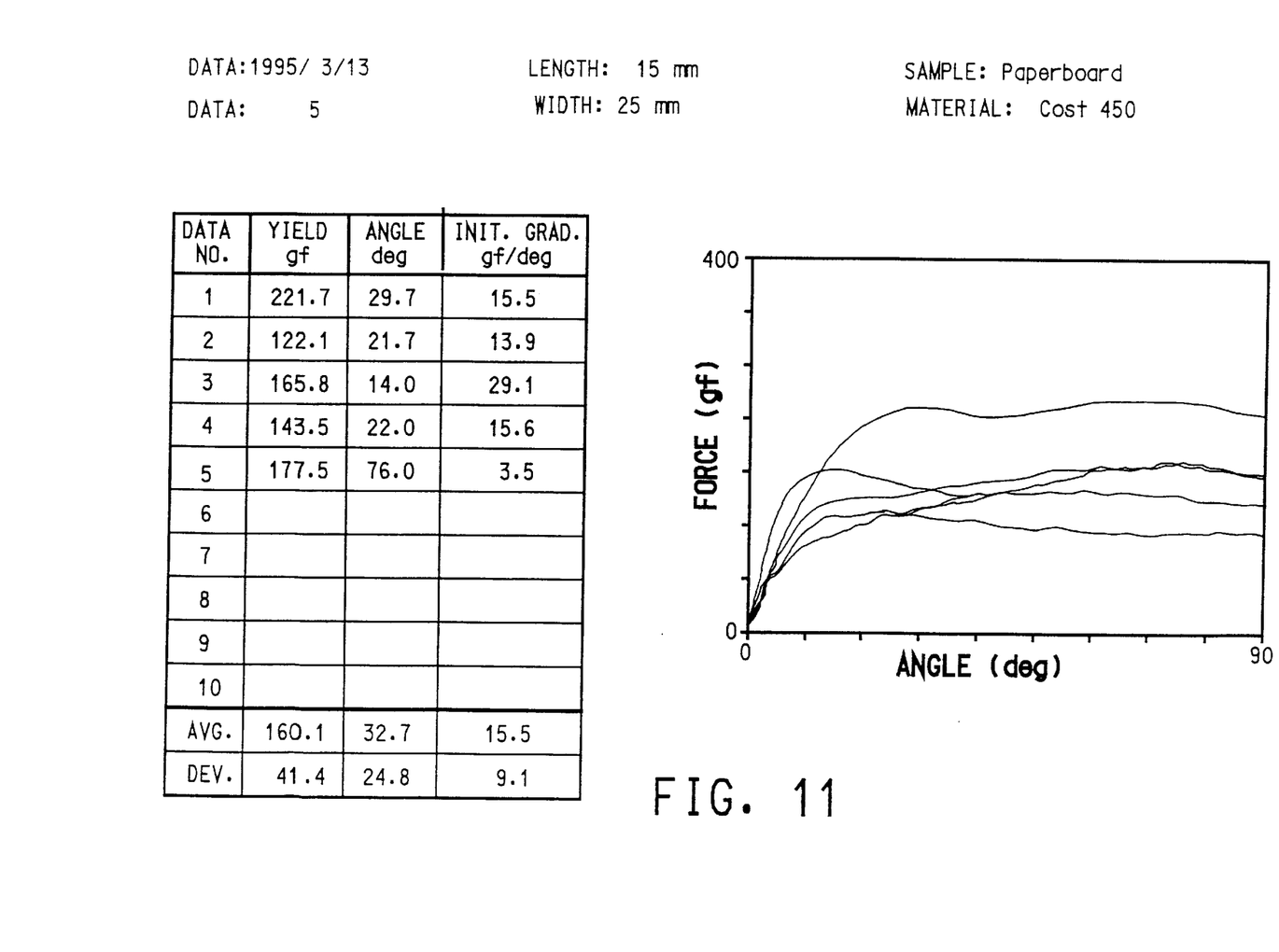
FIG. 11 is a graphical representation of the results obtained by the measurement performed by the device of FIG. 7.

FIG. 11 shows the results of the measurement under the same condition as that of FIG. 9 except that the results were obtained by measuring bending strength of the blank portion (data No. 1), creased portion (data Nos. 2 and 3), and perforated portion (data Nos. 4 and 5) of the paperboard.

In the device of the present invention, the handle 18 can be manually revolved to bend the sample material. However, the results of the measurement are not affected by the bending rate if the speed of revolution of the handle is less than about 50 degree/second. Just as in the case of the aforementioned embodiment, it is possible to make an assessment of yielding strength of the creased portion, warping force of the folded creased portion, mechanical characteristics of the creased portion, and so on.

By accumulating and analyzing the data from the various tests, the bending strength of a sheet material can be determined. The bending strength of the sheet material can then be used to determine the strength of a container made from the sheet material, by using the yielding value of the bending of the blank portion. Thus a device of the present invention will provide information regarding the strength of a sheet material that can be used to set up and adjust a process whereby a container is formed from such sheet material and then filled. By providing a means of obtaining such information, the present invention can be used to reduce the incidence of containers becoming entangled with packaging equipment in an assembly line, and to reduce the incidence of jamming during the formation of containers from the sheet material.

I claim:

1. A device for bending sheet material corrugated fiber board and paper board and measuring the force required to naturally crease the material as it is bent, comprising:

a. a clamp for securing one end of the sheet material, the clamp having a tip that extends perpendicularly to the predetermined bending direction;

b. a load sensor positioned to contact a portion of the sheet material;

c. a means for rotating the clamp;

d. a means for determining the angle of clamp rotation necessary to cause the sheet material to crease;

e. a means for measuring the force required to naturally crease the sheet material by dynamically analyzing data obtained from the load sensor and the means for determining the angle of clamp rotation; and f. a means for displaying the data.

2. A device of claim 1 wherein the means for rotating the clamp is a handle operatively connected to the clamp.

3. A device of claim 1 wherein the means for rotating the clamp is capable of rotating the clamp in a predetermined angle of from greater than about 90° to less than about 180°.

4. A device of claim 1 wherein the means for measuring the test data is removably connected to the device.

5. A device of claim 4 wherein the means for measuring the test data is capable of being connected to and communicating with a computer.

6. A device of claim 1 wherein the means for displaying the test data includes a printer.

7. A device of claim 1 wherein the sheet material is selected from the group comprising corrugated fiberboard, paperboard, and cardboard.

8. A device of claim 1 wherein the position of the load sensor is adjustable with respect to the clamp.

9. A device of claim 1 wherein the means for determining the angle of clamp rotation necessary to cause the sheet material to crease is an angular displacement sensor.

10. A device of claim 1 wherein the load sensor is operatively connected to the clamp and positioned to directly contact the sheet material.

11. A device of claim 1 for measuring the force required to naturally crease an unscored, blank sheet material.

12. A portable device for bending sheet material selected from corrugated fiber board and paper board and measuring the force required to naturally crease the material as it is bent, comprising:

a. a clamp for securing one end of the sheet material, the clamp having a tip that extends perpendicularly to the predetermined bending direction;

b. a load sensor positioned to contact a portion of the sheet material;

c. a means for rotating the clamp;

d. a means for determining the angle of clamp rotation necessary to cause the sheet material to crease;

e. a means for measuring the force required to naturally crease the sheet material by dynamically analyzing data obtained from the load sensor and the means for determining the angle of clamp rotation; and f. a means for displaying the data.

13. A device of claim 12 for measuring the force required to naturally crease an unscored, blank sheet material.

* * * * *

UNITED STATES PATENT AND TRADEMARK OFFICE
CERTIFICATE OF CORRECTION

PATENT NO. : 6,050,149
DATED : April 18, 2000
INVENTOR(S) : Akinori Yoshizawa

It is certified that error appears in the above-identified patent and that said Letters Patent is hereby corrected as shown below:

<u>Title page,</u>
After Item [76], insert -- [73] Assignee- Yoshizawa Industry, Inc., Niigata, Japan --

Signed and Sealed this

Twenty-sixth Day of August, 2003

JAMES E. ROGAN
*Director of the United States Patent and Trademark Office*